(12) United States Patent
Lu et al.

(10) Patent No.: US 11,229,675 B2
(45) Date of Patent: Jan. 25, 2022

(54) THERAPEUTIC PEPTIDES FOR EXCITATORY NEUROTOXICITY-RELATED INJURIES

(71) Applicant: Biocells (Beijing) Biotech Co., Ltd., Beijing (CN)

(72) Inventors: Ying Lu, Beijing (CN); Huamin Han, Beijing (CN)

(73) Assignee: Biocells (Beijing) Biotech Co., Ltd., Fengtai (CN)

( * ) Notice: Subject to any disclaimer, the term of this patent is extended or adjusted under 35 U.S.C. 154(b) by 155 days.

(21) Appl. No.: 16/096,877

(22) PCT Filed: Apr. 27, 2016

(86) PCT No.: PCT/CN2016/080321
§ 371 (c)(1),
(2) Date: Oct. 26, 2018

(87) PCT Pub. No.: WO2017/185249
PCT Pub. Date: Nov. 2, 2017

(65) Prior Publication Data
US 2019/0134143 A1 May 9, 2019

(51) Int. Cl.
| *A61K 38/08* | (2019.01) |
| *A61P 9/10* | (2006.01) |
| *A61P 25/16* | (2006.01) |
| *A61P 25/28* | (2006.01) |
| *C07K 7/06* | (2006.01) |
| *A61P 9/00* | (2006.01) |

(52) U.S. Cl.
CPC ............... *A61K 38/08* (2013.01); *A61P 9/00* (2018.01); *A61P 9/10* (2018.01); *A61P 25/16* (2018.01); *A61P 25/28* (2018.01); *C07K 7/06* (2013.01); *C07K 2319/01* (2013.01)

(58) Field of Classification Search
None
See application file for complete search history.

(56) References Cited

U.S. PATENT DOCUMENTS

| 9,161,965 B2 | 10/2015 | Gurd et al. | |
| 2005/0019841 A1 | 1/2005 | Garman et al. | |
| 2005/0059597 A1 | 3/2005 | Tymianski | |
| 2006/0073161 A1* | 4/2006 | Breton | C07K 14/195 424/190.1 |
| 2006/0148711 A1 | 7/2006 | Lu et al. | |
| 2008/0193470 A1* | 8/2008 | Masignani | C07K 16/1232 424/185.1 |
| 2013/0121915 A1* | 5/2013 | Paas | B82Y 5/00 424/9.1 |
| 2013/0156704 A1 | 6/2013 | Tymianski | |
| 2017/0121381 A1* | 5/2017 | Offen | C07K 14/47 |

FOREIGN PATENT DOCUMENTS

| CN | 101134780 A | 3/2008 | |
| CN | 101827604 A | 9/2010 | |
| CN | 107312069 B | 11/2018 | |
| CN | 109718363 B | 12/2019 | |
| EP | 2 175 873 B1 | 11/2015 | |
| EP | 2 616 094 B1 | 11/2017 | |
| WO | WO 2009/006548 A2 | 1/2009 | |
| WO | WO 2009/140416 A2 | 11/2009 | |
| WO | WO 2010/004003 A2 | 1/2010 | |
| WO | WO 2010/144721 A2 | 12/2010 | |
| WO | WO 2012/021854 A2 | 2/2012 | |
| WO | WO 2012/176172 A1 | 12/2012 | |
| WO | WO-2014057484 A1 * | 4/2014 | ......... C07K 14/8139 |
| WO | WO 2018/103038 A1 | 6/2018 | |

OTHER PUBLICATIONS

Bratane et al., "Neuroprotection by Freezing Ischemic Penumbra Evolution Without Cerebral Blood Flow Augmentation With a Postsynaptic Density-95 Protein Inhibitor," *Stroke*, 42(11): 3265-3270 (2011).
Cook et al., "Treatment of stroke with a PSD-95 inhibitor in the gyrencephalic primate brain," *Nature*, 483(7388): 213-217 (2012).
European Patent Office, Extended European Search Report in European Patent Application No. 16899763.3, dated Mar. 15, 2019.
Sun et al., "Effectiveness of PSD95 Inhibitors in Permanent and Transient Focal Ischemia in the Rat," *Stroke*, 39(9): 2544-2553 (2008).
Al-Obeidi et al., "Peptide and Peptidomimetic Libraries," *Mol. Biotechnol.*, 9: 205-223 (1998).
Cui et al., "PDZ Protein Interactions Underlying NMDA Receptor-Mediated Excitotoxicity and Neuroprotection by PSD-95 Inhibitors," *The J. of Neuroscience*, 27(37): 9901-9915 (2007).
Doyle et al., "Crystal Structures of a Complexed and Peptide-Free Membrane Protein-Binding Domain: Molecular Basis of Peptide Recognition by PDZ," *Cell*, 85: 1067-1076 (1996).
GenBank Accession No. U88963.1 (printed Jan. 5, 1999).
Hruby et al., "Synthesis of oligopeptide and peptidomimetic libraries," *Curr. Opin. Chem. Biol.*, 1:114-119 (1997).

(Continued)

*Primary Examiner* — Daniel E Kolker
*Assistant Examiner* — Aditi Dutt
(74) *Attorney, Agent, or Firm* — Leydig, Voit & Mayer

(57) ABSTRACT

There is provided in the present application a peptide comprising the amino acid sequence of YEKLLDTEI (SEQ ID NO: 1) or a functional variant thereof. The peptide is an active peptide for the treatment of a central nervous system injury. The present application also provides a chimeric peptide comprising an active peptide and an internalization peptide. The present application also provides a pharmaceutical composition comprising the active peptide or the chimeric peptide, as well as medical use of the active peptide or the chimeric peptide.

22 Claims, 3 Drawing Sheets
Specification includes a Sequence Listing.

(56) References Cited

OTHER PUBLICATIONS

International Bureau, International Search Report in International Application No. PCT/CN2016/080321, dated Jan. 9, 2017.
International Bureau, Written Opinion in International Application No. PCT/CN2016/080321, dated Jan. 9, 2017.
Lees et al., "NXY-059 for Acute Ischemic Stroke," *N. Engl. J. Med.*, 354: 588-600 (2006).
Mahoney et al., "Functional Evaluation: The Barthel Index," *Maryland State Med. J.*, 14:56-61 (1965).
Ouyang et al., "Neuroprotection by PSD-95 inhibitors after ischemic brain injuries," *Chin. J. Nerv. Ment. Dis.*, 41(6): 380-382 (2015).
Ostergaard et al., "Peptomers: A versatile approach for the preparation of diverse combinatorial peptidomimetic bead libraries," *Mol. Divers.*, 3: 17-27 (1997).
Ostresh et al., "Generation and Use of Nonsupport-Bound Peptide and Peptidomimetic Combinatorial Libraries," *Methods Enzymol.*, 267: 220-234 (1996).
Rankin, J., "Cerebral Vascular Accidents in Patients Over the Age of 60: II. Prognosis," *Scot. Med. J.*, 2: 200-215 (1957).
Aarts, et al., "Treatment of Ischemic Brain Damage by Perturbing NMDA Receptor—PSD-95 Protein Interactions," *Science*, 298, 846-850 (2002).
Arundine et al., "Molecular mechanisms of glutamate-dependent neurodegeneration in ischemia and traumatic brain injury," *CMLS, Cell. Mol. Life Sci.*, 61 (2004) 657-668.
Bustos et al., "Epigenetic editing of the Dlg4/PSD95 gene improves cognition in aged and Alzheimer's disease mice," *Brain* 2017: 140; 3252-3268.
Caccamo et al., "Reducing Ribosomal Protein S6 Kinase 1 Expression Improves Spatial Memory and Synaptic Plasticity in a Mouse Model of Alzheimer's Disease," *J. Neurosci.*, Oct. 14, 2015, 35(41): 14042-14056.
Fan, J. et al., "Interaction of Postsynaptic Density Protein-95 with NMDA Receptors Influences Excitotoxicity in the Yeast Artificial Chromosome Mouse Model of Huntington's Disease," *J. Neurosci.*, Sep. 2, 2009, 29(35): 10928-10938.
Park, H. et al., "Mice lacking the PSD-95-interacting E3 ligase, Dorfin/Rnf19a, display reduced adult neurogenesis, enhanced long-term potentiation, and impaired contextual fear conditioning," *Sci. Rep.* 5, 16410; doi: 10.1038/srep16410 (2015).
Yin, XH et al., "PDZ1 inhibitor peptide protects neurons against ischemia via inhibiting GluK2-PSD-95-module-mediated Fas signaling pathway," *Brain Research* 1637 (2016) 64-70.
Bach et al., "A high-affinity, dimeric inhibitor of PSD-95 bivalently interacts with PDZ1-2 and protects against ischemic brain damage," *PNAS*, vol. 109, No. 9 pp. 3317-3322 (2012).

\* cited by examiner

SEQUENCE LISTING

```
<160> NUMBER OF SEQ ID NOS: 45

<210> SEQ ID NO 1
<211> LENGTH: 9
<212> TYPE: PRT
<213> ORGANISM: Artificial Sequence
<220> FEATURE:
<223> OTHER INFORMATION: P5 active peptide

<400> SEQUENCE: 1

Tyr Glu Lys Leu Leu Asp Thr Glu Ile
1               5

<210> SEQ ID NO 2
<211> LENGTH: 11
<212> TYPE: PRT
<213> ORGANISM: Artificial Sequence
<220> FEATURE:
<223> OTHER INFORMATION: Tat internalization peptide

<400> SEQUENCE: 2

Tyr Gly Arg Lys Lys Arg Arg Gln Arg Arg Arg
1               5                   10

<210> SEQ ID NO 3
<211> LENGTH: 20
<212> TYPE: PRT
<213> ORGANISM: Artificial Sequence
<220> FEATURE:
<223> OTHER INFORMATION: P5 chimeric peptide

<400> SEQUENCE: 3

Tyr Gly Arg Lys Lys Arg Arg Gln Arg Arg Tyr Glu Lys Leu Leu
1               5                   10                  15

Asp Thr Glu Ile
            20

<210> SEQ ID NO 4
<211> LENGTH: 20
<212> TYPE: PRT
<213> ORGANISM: Artificial Sequence
<220> FEATURE:
<223> OTHER INFORMATION: NA-1

<400> SEQUENCE: 4

Tyr Gly Arg Lys Lys Arg Arg Gln Arg Arg Arg Lys Leu Ser Ser Ile
1               5                   10                  15
```

```
Glu Ser Asp Val
        20

<210> SEQ ID NO 5
<211> LENGTH: 22
<212> TYPE: PRT
<213> ORGANISM: Artificial Sequence
<220> FEATURE:
<223> OTHER INFORMATION: YE-NA-1

<400> SEQUENCE: 5

Tyr Gly Arg Lys Lys Arg Arg Gln Arg Arg Tyr Glu Lys Leu Ser
1               5                   10                  15

Ser Ile Glu Ser Asp Val
            20

<210> SEQ ID NO 6
<211> LENGTH: 5
<212> TYPE: PRT
<213> ORGANISM: Artificial Sequence
<220> FEATURE:
<223> OTHER INFORMATION: LDTEI segment of SEQ ID NO: 1

<400> SEQUENCE: 6

Leu Asp Thr Glu Ile
1               5

<210> SEQ ID NO 7
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 7

Leu Asp Thr Glu Leu
1               5

<210> SEQ ID NO 8
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 8

Leu Asp Thr Glu Val
1               5

<210> SEQ ID NO 9
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 9

Leu Asp Thr Asp Ile
1               5

<210> SEQ ID NO 10
<211> LENGTH: 5
<212> TYPE: PRT
<213> ORGANISM: Artificial Sequence
<220> FEATURE:
<223> OTHER INFORMATION: variant of LDTEI segment
```

<400> SEQUENCE: 10

Leu Asp Thr Asp Leu
1               5

<210> SEQ ID NO 11
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 11

Leu Asp Thr Asp Val
1               5

<210> SEQ ID NO 12
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 12

Leu Asp Ser Glu Ile
1               5

<210> SEQ ID NO 13
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 13

Leu Asp Ser Glu Leu
1               5

<210> SEQ ID NO 14
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 14

Leu Asp Ser Glu Val
1               5

<210> SEQ ID NO 15
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 15

Leu Asp Ser Asp Ile
1               5

<210> SEQ ID NO 16
<211> LENGTH: 5
<212> TYPE: PRT
<213> ORGANISM: Artificial Sequence
<220> FEATURE:
<223> OTHER INFORMATION: variant of LDTEI segment

```
<400> SEQUENCE: 16

Leu Asp Ser Asp Leu
1               5

<210> SEQ ID NO 17
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 17

Leu Asp Ser Asp Val
1               5

<210> SEQ ID NO 18
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 18

Leu Glu Thr Glu Ile
1               5

<210> SEQ ID NO 19
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 19

Leu Glu Thr Glu Leu
1               5

<210> SEQ ID NO 20
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 20

Leu Glu Thr Glu Val
1               5

<210> SEQ ID NO 21
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 21

Leu Glu Thr Asp Ile
1               5

<210> SEQ ID NO 22
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 22
```

```
Leu Glu Thr Asp Leu
1               5

<210> SEQ ID NO 23
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 23

Leu Glu Thr Asp Val
1               5

<210> SEQ ID NO 24
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 24

Val Asp Thr Glu Ile
1               5

<210> SEQ ID NO 25
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 25

Val Asp Thr Glu Leu
1               5

<210> SEQ ID NO 26
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 26

Val Asp Thr Glu Val
1               5

<210> SEQ ID NO 27
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 27

Val Asp Thr Asp Ile
1               5

<210> SEQ ID NO 28
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 28
```

Val Asp Thr Asp Leu
1               5

<210> SEQ ID NO 29
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 29

Val Asp Thr Asp Val
1               5

<210> SEQ ID NO 30
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 30

Ile Asp Thr Glu Ile
1               5

<210> SEQ ID NO 31
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 31

Ile Asp Thr Glu Leu
1               5

<210> SEQ ID NO 32
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 32

Ile Asp Thr Glu Val
1               5

<210> SEQ ID NO 33
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 33

Ile Asp Thr Asp Ile
1               5

<210> SEQ ID NO 34
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 34

Ile Asp Thr Asp Leu

```
1               5

<210> SEQ ID NO 35
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 35

Ile Asp Thr Asp Val
1               5

<210> SEQ ID NO 36
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 36

Ile Glu Thr Glu Ile
1               5

<210> SEQ ID NO 37
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 37

Ile Glu Thr Glu Leu
1               5

<210> SEQ ID NO 38
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 38

Ile Glu Thr Glu Val
1               5

<210> SEQ ID NO 39
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 39

Ile Glu Thr Asp Ile
1               5

<210> SEQ ID NO 40
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 40

Ile Glu Thr Asp Leu
1               5
```

```
<210> SEQ ID NO 41
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 41

Ile Glu Thr Asp Val
1               5

<210> SEQ ID NO 42
<211> LENGTH: 20
<212> TYPE: PRT
<213> ORGANISM: Homo sapiens

<400> SEQUENCE: 42

Phe Asn Gly Ser Ser Asn Gly His Val Tyr Glu Lys Leu Ser Ser Leu
1               5                   10                  15

Glu Ser Asp Val
            20

<210> SEQ ID NO 43
<211> LENGTH: 4
<212> TYPE: PRT
<213> ORGANISM: Homo sapiens

<400> SEQUENCE: 43

Glu Ser Asp Val
1

<210> SEQ ID NO 44
<211> LENGTH: 5
<212> TYPE: PRT
<213> ORGANISM: Homo sapiens

<400> SEQUENCE: 44

Leu Glu Ser Asp Val
1               5

<210> SEQ ID NO 45
<211> LENGTH: 4
<212> TYPE: PRT
<213> ORGANISM: Homo sapiens

<400> SEQUENCE: 45

Tyr Glu Lys Leu
1
```

THERAPEUTIC PEPTIDES FOR EXCITATORY NEUROTOXICITY-RELATED INJURIES

CROSS-REFERENCE TO RELATED APPLICATIONS

This patent application is the U.S. National Stage of International Patent Application No. PCT/CN2016/080321, filed Apr. 27, 2016, which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,093 Byte ASCII (Text) file named "740978.TXT," dated Nov. 30, 2018.

TECHNICAL FIELD

The present application generally relates to the medical field. In particular, there is provided in the present application peptides, compositions, and methods for treating central nervous system injuries.

BACKGROUND OF THE INVENTION

Stroke is a common acute cerebrovascular disease in middle-aged and elderly people, and tends to attack the younger. It is one of the top three diseases (cancers, cardiovascular diseases and diabetes) harmful to humans in the world today. Nearly three million people die from cerebrovascular diseases every year in China. This number is 4 to 5 times higher than that of the US and European countries, 3.5 times higher than that of Japan, and even higher than that of developing countries such as Thailand and India. The incidence rate increases at a rate of 8.7% per year. The recurrence rate exceeds 30%, and the rate of recurrence within five years reaches 54%. 75% of stroke survivors lose their labor capacity and 40% are severely disabled.

Stroke can be roughly divided into two categories, namely ischemic stroke and hemorrhagic stroke, of which ischemic stroke accounts for 85% of the total number of stroke patients. At present, therapeutic drugs for ischemic stroke mainly includes the following types: vasodilators (such as persantine), drugs that improve microcirculation and expand blood volume (such as low molecular dextran), thrombolytic drugs (such as urokinase), anticoagulant drugs, drugs that prevent platelet aggregation (such as aspirin), Chinese medicine, neuroprotective agents, etc. However, because most of these drugs have issues like significant side effects, potential risks, or insufficient therapeutic efficiency, study on the pathogenesis of stroke and development of drugs directed to the pathogenesis have important social significance for the prevention and treatment of occurrence and development of cerebrovascular diseases.

Stroke is characterized by neuronal cell death in the regions of local ischemia, cerebral hemorrhage, and/or trauma. Neuron death or injuries caused by cerebral ischemia undergo an injury cascade process, i.e., after occurrence of cerebral ischemia, tissue blood perfusion decreases, excitatory neurotransmitters increase which in turn activates NMDA and AMPA receptors, causes ion channel opening and calcium ion influx, and further activates a large number of enzymes to trigger a signal cascade, resulting in nerve cell damage via multiple pathways. Downstream postsynaptic density 95 protein (PSD-95) triggers a series of ischemic injuries through interaction with various proteins, and therefore is a critical factor for injuries caused by cerebral ischemia, and also a potential target for drug therapy. Therefore, development of PSD-95 inhibitors has great medical significance to nervous system injuries caused by various excitatory neurotoxicity including stroke.

In addition, studies have shown that excitatory neurotransmitter NMDA plays an important role in anxiety, epilepsy, and various neurodegenerative diseases such as Alzheimer's disease, amyotrophic lateral sclerosis (ALS), Parkinson's disease, or Huntington's disease. For example, studies have shown that excessive excitation of the central glutamatergic system can cause anxiety, while the NMDA receptor (NMDAR) is a major part responsible for glutamic acid excitatory neurotoxicity. The onset of epilepsy includes three different but continuous pathophysiological processes, including initiation, maintenance and expansion of seizure discharge, and inhibition of seizure discharge. During this process, excitatory neurotransmitters, such as glutamic acid and aspartic acid, play an important role. In Alzheimer's disease, PSD-95 is involved in the neurotoxic mechanism of the disease through the GluR6-PSD-95-MLK3 pathway. Furthermore, in Huntington's disease, PSD-95 is a mediator of neurotoxicity caused by NMDA receptors and huntingtin mutants. Therefore, development of PSD-95 inhibitors is also important for the treatment, amelioration and prevention of the above diseases.

SUMMARY OF THE INVENTION

In a first aspect, there is provided in the present application a peptide comprising the amino acid sequence YEKLL-DTEI (SEQ ID NO: 1) or a functional variant thereof.

In some embodiments, the functional variant is a variant generated by one or more conservative substitutions in the LDTEI (SEQ ID NO: 6) segment of SEQ ID NO: 1.

In some embodiments, the conservative substitution is selected from the group consisting of a substitution between D and E, a substitution among L, V and I, and a substitution between T and S.

In some embodiments, the functional variant is a variant generated by replacing the LDTEI (SEQ ID NO: 6) segment of SEQ ID NO: 1 with a sequence selected from the group consisting of LDTEL (SEQ ID NO: 7), LDTEV (SEQ ID NO: 8), LDTDI (SEQ ID NO: 9), LDTDL (SEQ ID NO: 10), LDTDV (SEQ ID NO: 11), LDSEI (SEQ ID NO: 12), LDSEL (SEQ ID NO: 13), LDSEV (SEQ ID NO: 14), LDSDI (SEQ ID NO: 15), LDSDL (SEQ ID NO: 16), LDSDV (SEQ ID NO: 17), LETEI (SEQ ID NO: 18), LETEL (SEQ ID NO: 19), LETEV (SEQ ID NO: 20), LETDI (SEQ ID NO: 21), LETDL (SEQ ID NO: 22), LETDV (SEQ ID NO: 23), VDTEI (SEQ ID NO: 24), VDTEL (SEQ ID NO: 25), VDTEV (SEQ ID NO: 26), VDTDI (SEQ ID NO: 27), VDTDL (SEQ ID NO: 28), VDTDV (SEQ ID NO: 29), IDTEI (SEQ ID NO: 30), IDTEL (SEQ ID NO: 31), IDTEV (SEQ ID NO: 32), IDTDI (SEQ ID NO: 33), IDTDL (SEQ ID NO: 34), IDTDV (SEQ ID NO: 35), IETEI (SEQ ID NO: 36), IETEL (SEQ ID NO: 37), IETEV (SEQ ID NO: 38), IETDI (SEQ ID NO: 39), IETDL (SEQ ID NO: 40), and IETDV (SEQ ID NO: 41).

In a second aspect, there is provided in the present application a chimeric peptide comprising an active peptide and an internalization peptide, wherein the active peptide is a peptide as described in the first aspect, and the internalization peptide is capable of facilitating uptake of the chimeric peptide by a cell.

In some embodiments, the internalization peptide comprises the amino acid sequence YGRKKRRQRRR (SEQ ID NO: 2).

In some embodiments, the chimeric peptide comprises the amino acid sequence YGRKKRRQRRRYEKLLDTEI (SEQ ID NO: 3).

In a third aspect, there is provided in the present application a pharmaceutical composition comprising a peptide as described in the first aspect or a chimeric peptide as described in the second aspect, and a pharmaceutically acceptable carrier.

In some embodiments, the pharmaceutical composition is used for treating a central nervous system injury or used as a neuroprotective agent.

In some embodiments, the pharmaceutical composition is used for treating a nervous system injury caused by ischemic stroke.

In a fourth aspect, there is provided in the present application a method for treating a central nervous system injury comprising administering a peptide as described in the first aspect, or a chimeric peptide as described in the second aspect, or a pharmaceutical composition as described in the third aspect, to a subject in need thereof.

In some embodiments, the subject is a subject suffering from ischemic stroke.

In a fifth aspect, there is provided in the present application use of a peptide as described in the first aspect, or a chimeric peptide as described in the second aspect, or a pharmaceutical composition as described in the third aspect, in the preparation of a medicament for treating a central nervous system injury or a neuroprotective agent.

In some embodiments, the medicament is used for treating a nervous system injury caused by ischemic stroke.

DETAILED DESCRIPTION OF THE INVENTION

Figure 1:
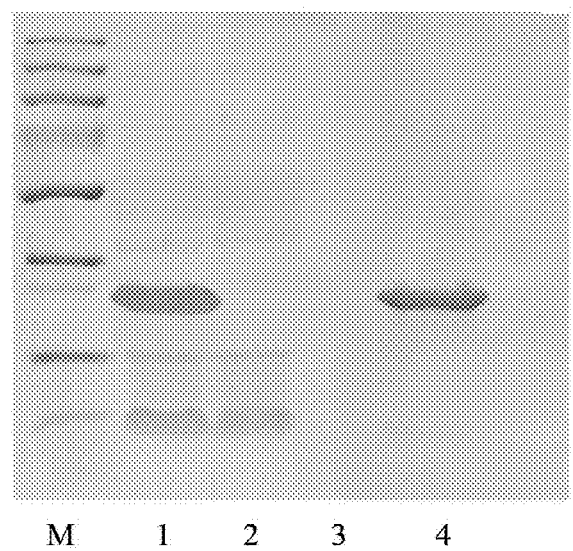
FIG. 1 shows the result of a pull-down assay to detect interaction between P5 and PDZ1/2 domain. M represents a protein molecular weight marker; Lane 1 shows His+PDZ1/2+P5; Lane 2 shows P5 alone; Lane 3 shows His+P5; and Lane 4 shows His+PDZ1/2. The eluted band shown in Lane 1 contains both P5 and PDZ1/2, confirming that P5 is capable of binding to PDZ1/2 domain.

The inventors of the present application have studied peptides that have been reported in the art to reduce the damaging effects of neurological disorders mediated at least in part by NMDAR excitatory neurotoxicity. Without wishing to be bound by any theory, it is believed that such peptides function, at least in part, by inhibiting the interaction between NMDAR and postsynaptic density 95 protein (PSD-95) (i.e., PSD-95 inhibitors). On the basis of the above, the inventors of the present application have intensively considered various targets for the treatment of ischemic stroke, designed and screened polypeptide neuroprotective agents via pharmacological and pharmacodynamics experiments in vivo and in vitro, and obtained peptides with desirable properties.

Definitions

Unless otherwise indicated, the terms used in the present application have the meaning as commonly understood by one of ordinary skill in the art.

The one-letter or three-letter abbreviations for amino acids used in the present application are consistent with international conventions.

The term "chimeric peptide" means a peptide having two peptide components which are not naturally associated with each other. The two peptide components can form a fusion protein or can be linked by a chemical bond.

The term "PDZ domain" refers to a modular protein domain of approximately 90 amino acids characterized by a high sequence identity (e.g., at least 60%) to a synaptic protein PSD-95, a *Drosophila* separating connexin Discs-Large (DLG), and an epithelial tight junction protein Z01. The PDZ domain is also known as Discs-Large homolog repeats ("DHRs") and GLGF repeats. The PDZ domain typically has retained a core consensus sequence (Doyle, D. A., 1996, Cell 85: 1067-76). Exemplary PDZ domain-containing proteins and PDZ domain sequences are disclosed in U.S. application Ser. No. 10/714,537.

The term "NMDA receptor" or "NMDAR" refers to a membrane associated protein known to interact with NMDA. These receptors can be human or non-human (e.g., from mice, rats, rabbits, or monkeys).

The term "specific binding" refers to binding between two molecules (e.g., a ligand and a receptor) characterized by one molecule (e.g., a ligand) being capable of binding to another specific molecule (e.g., a receptor) even in the presence of many other different molecules, i.e. the ability of one molecule to preferentially bind to another molecule in a heterogeneous molecule mixture. The specific binding of a ligand to a receptor can also confirmed where the binding of a detectably labeled ligand to a receptor is reduced when excess unlabeled ligands are present (i.e., a binding competition assay).

The term "statistically significant" means a p value <0.05, preferably <0.01, most preferably <0.001.

The term "functional variant" refers to a variant having same or similar biological function and property as the parent. As a non-limiting example, a "functional variant" can be obtained by performing one or more conservative substitutions in the parent.

An "internalization peptide", also known as a cell-penetrating peptide, is widely used in the field of protein drugs and functions to facilitate the uptake and absorption of an active peptide bound thereto by cells. As a non-limiting example, an internalization peptide can be a Tat peptide. One non-limiting example of Tat peptides is YGRKKRRQRRR (SEQ ID NO: 2).

In a first aspect, there is provided in the present application a peptide comprising the amino acid sequence YEKLLDTEI (SEQ ID NO: 1) or a functional variant thereof. The peptide is also referred to herein as an "active peptide", which acts as an active moiety in the chimeric peptides of the present application for the treatment of a central nervous system injury or use as a neuroprotective agent.

According to existing studies, some active peptides that inhibit the interaction between NMDAR and PSD-95 are based on the structure of NMDAR. For example, NMDAR2B (GenBank ID 4099612) has 20 amino acids FNGSSNGHVYEKLSSLESDV (SEQ ID NO: 42) at its C-terminus and the PL motif ESDV (SEQ ID NO: 43). Some known active peptides contain a part of the amino acid sequence at the C-terminus of NMDAR2B, thereby competitively inhibiting PSD-95 with NMDAR2B. Studies have suggested that the ESDV (SEQ ID NO: 43) or LESDV (SEQ ID NO: 44) segment in the above peptides plays an important role in inhibiting the interaction between NMDAR and PSD-95 Without being bound by any theory, the inventors of the present application have surprisingly discovered that the alterations of the active peptide YEKLLDTEI (SEQ ID NO: 1) disclosed herein as compared with the amino acid composition at the C-terminus of the above NMDAR2B (lacking two residues SS following KL while having the amino acid sequence YEKL (SEQ ID NO: 45) extending from the N-terminus of the PL motif) enhance the interaction of an active peptide with the PDZ1/2 domain. At the same time, the LDTEI (SEQ ID NO: 6) segment at the C-terminus of the peptide relative to the YEKL (SEQ ID NO: 45) motif can be modified, and it is expected that such a modification does not affect the activity of the active peptide or may even increase its activity. Accordingly, in some embodiments, the functional variant provided herein is a variant generated by one or more conservative substitutions in the LDTEI (SEQ ID NO: 6) segment of SEQ ID NO: 1.

In some embodiments, the conservative substitution is selected from the group consisting of a substitution between D and E, a substitution among L, V and I, and a substitution between T and S.

In some more particular embodiments, the functional variant is a variant generated by replacing the LDTEI (SEQ ID NO: 6) segment of SEQ ID NO: 1 with a sequence selected from the group consisting of LDTEL (SEQ ID NO: 7), LDTEV (SEQ ID NO: 8), LDTDI (SEQ ID NO: 9), LDTDL (SEQ ID NO: 10), LDTDV (SEQ ID NO: 11), LDSEI (SEQ ID NO: 12), LDSEL (SEQ ID NO: 13), LDSEV (SEQ ID NO: 14), LDSDI (SEQ ID NO: 15), LDSDL (SEQ ID NO: 16), LDSDV (SEQ ID NO: 17), LETEI (SEQ ID NO: 18), LETEL (SEQ ID NO: 19), LETEV (SEQ ID NO: 20), LETDI (SEQ ID NO: 21), LETDL (SEQ ID NO: 22), LETDV (SEQ ID NO: 23), VDTEI (SEQ ID NO: 24), VDTEL (SEQ ID NO: 25), VDTEV (SEQ ID NO: 26), VDTDI (SEQ ID NO: 27), VDTDL (SEQ ID NO: 28), VDTDV (SEQ ID NO: 29), IDTEI (SEQ ID NO: 30), IDTEL (SEQ ID NO: 31), IDTEV (SEQ ID NO: 32), IDTDI (SEQ ID NO: 33), IDTDL (SEQ ID NO: 34), IDTDV (SEQ ID NO: 35), IETEI (SEQ ID NO: 36), IETEL (SEQ ID NO: 37), IETEV (SEQ ID NO: 38), IETDI (SEQ ID NO: 39), IETDL (SEQ ID NO: 40), and IETDV (SEQ ID NO: 41).

In some embodiments, the functional variants disclosed herein also comprise an amino acid sequence having at least 60%, 70%, 75%, 80%, 85%, 90%, 95%, or even higher identity to the peptides as mentioned above. It is known in the art that "identity" between two proteins can be determined by aligning the amino acid sequence of a first protein with the sequence of a second protein which comprises a conservative amino acid substitution relative to the first protein. The degree of identity between two proteins can be determined using computer algorithms and methods well-known to those skilled in the art. The identity between two amino acid sequences is preferably determined by using the BLASTP algorithm.

In some embodiments, the functional variants disclosed herein include those having substitutions, deletions, additions and/or insertions of amino acid residues at 1, 2, 3, 4, 5 or more positions as compared with the peptides as mentioned above, thereby differing from the particular peptides disclosed above.

As described above, a functional variant can differ from a particular peptide disclosed above in one or more substitutions, deletions, additions, and/or insertions. Such variants may be naturally occurring or synthetically produced. For example, one or more of the above-described peptide sequences disclosed herein can be modified and their biological activities can be evaluated following any of a variety of techniques well-known in the art as described herein.

In a second aspect, there is provided in the present application a chimeric peptide comprising an active peptide and an internalization peptide, wherein the active peptide is a peptide as described in the first aspect, and the internalization peptide is capable of facilitating uptake of the chimeric peptide by a cell.

It should be understood by those skilled in the art that the main purpose of incorporating an active peptide and an internalization peptide into a chimeric peptide is to better deliver the active peptide to the target of action. Therefore, internalization peptides suitable for the present application are not limited to specific types, as long as the cell-penetrating purpose can be achieved. It should also be understood by those skilled in the art that since the targets of action of the active peptide are mainly located inside neuronal cells, it is preferred that the internalization peptide is specifically appropriate to neuronal cells. In some embodiments, the internalization peptide can be a Tat peptide. In some embodiments, the amino acid sequence of a Tat peptide is YGRKKRRQRRR (SEQ ID NO: 2). In some embodiments, the chimeric peptide comprises the amino acid sequence YGRKKRRQRRRYEKLLDTEI (SEQ ID NO: 3).

It should be appreciated that an internalization peptide may be linked to an active peptide via an amide bond to form a fusion peptide, but they may also be linked via other suitable means, such as chemical bonding. Coupling of two components can be achieved with a coupling agent or a conjugating agent. A great number of such reagents are commercially available and can be found in S. S. Wong, Chemistry of Protein Conjugation and Cross-Linking, CRC Press (1991). Some examples of cross-linking reagents include J-succinimide-3-(2-pyridinedithio)propionate (SPOP) or N,N'-(1,3-phenylene) bismaleimide; N, N'-ethylidene-bis-(iodoacetamide) or other such reagents having 6 to 11 carbon methylene bridges (which are relatively specific to thiol groups); and 1,5-difluoro-2,4-dinitrobenzene (which forms an irreversible linkage with an amino group and an tyrosine group). Other cross-linking reagents include P,P'-difluoro-m,m'-dinitrodiphenyl sulfone (which forms an irreversible cross-linkage with an amino group and an phenol group); dimethyl diethylamine hexanoate (which is specific to an amino group); phenol-1,4-disulfonyl chloride (which mainly reacts with an amino group); 1,6-hexamethylene diisocyanate or diisothiocyanate, or phenylazo-p-diisocyanate (which mainly reacts with an amino group; glutaraldehyde (which reacts with several different side chains) and bis-diazotized benzidine (which mainly reacts with tyrosine and histidine).

Furthermore, the peptides as described above can optionally be derivatized (e.g., acetylated, phosphorylated, and/or glycosylated) to promote their affinity to inhibitors, promote the transport ability of inhibitors across cell membranes, or promote their stability.

The active peptide and the fusion peptide in which the active peptide is fused to an internalization peptide of the present application can be synthesized by solid phase synthesis methods or recombinant methods. Peptidomimetics can be synthesized using a variety of protocols and methods described in scientific literatures and patent literatures, such as Organic Syntheses Collective Volumes, Gilman et al. (ed.) John Wiley & Sons, Inc., NY, al-Obeidi (1998) Mol. Biotechnol. 9:205-223; Hruby (1997) Curr. Opin. Chem. Biol. 1: 114-119; Ostergaard (1997) Mol. Divers. 3: 17-27; Ostresh (1996) Methods Enzymol. 267: 220-234.

In a third aspect, there is provided in the present application a pharmaceutical composition comprising a peptide as described in the first aspect or a chimeric peptide as described in the second aspect, and a pharmaceutically acceptable carrier.

In some embodiments, the active peptides or chimeric peptides disclosed herein can be administered in the form of a pharmaceutical composition. The pharmaceutical composition can be prepared by conventional methods, e.g., mixing, dissolving, granulating, tableting, milling, emulsifying, encapsulating, capturing or lyophilizing.

The pharmaceutical composition can be formulated in a conventional manner using one or more physiologically acceptable carriers, diluents, excipients or ingredients suitable for preparing the active peptide or chimeric peptide into a pharmaceutically acceptable formulation. Proper formulation depends on chosen administration routes.

In some embodiments, the administration can be parenteral, intravenous, oral, subcutaneous, intraarterial, intracranial, intrathecal, intraperitoneal, topical, intranasal, or intramuscular administration. Intravenous administration is preferred.

In some embodiments, the pharmaceutical composition for parenteral administration is preferably sterile and substantially isotonic. For injection, the active peptide or chimeric peptide can be formulated in an aqueous solution, preferably in a physiologically compatible buffer such as Hank's solution, Ringer's solution, or physiological saline or acetate buffer (to reduce discomfortableness at injection sites). The solution may contain formulating agents such as suspending, stabilizing and/or dispersing agents.

Alternatively, the active peptide or chimeric peptide may be in the form of a powder for re-constitution with a suitable carrier, such as sterile non-pyrogenic water, prior to use.

For transmucosal administration, penetrants appropriate for penetrating the barrier of interest are used in the formulation. This administration route can be used to deliver a compound to the nasal cavity or for sublingual administration.

In some embodiments, for oral administration, the active peptide or chimeric peptide can be formulated with a pharmaceutically acceptable carrier into tablets, pills, troches, capsules, liquids, gels, syrups, slurries, suspensions or the like, for oral ingestion by a patient to be treated. For oral solid formulations such as powders, capsules and tablets, suitable excipients include fillers such as sugars such as lactose, sucrose, mannitol and sorbitol; cellulose preparations such as corn starch, wheat starch, rice starch, potato starch, gelatin, tragacanth, methylcellulose, carboxypropylmethylcellulose, sodium carboxymethylcellulose and/or povidone (PVP); granulating agents and binders. If necessary, a disintegrating agent, such as crosslinked polyvinylpyrrolidone, agar, or alginic acid or a salt thereof (such as sodium alginate), may be added. If necessary, the solid formulations can be coated with sugar or enteric coating using standard techniques. For oral liquid preparations such as suspensions, elixirs and solutions, suitable carriers, excipients or diluents include water, glycerol, oil and alcohol. Furthermore, a flavoring agent, a preservative, a coloring agent, or the like may be added.

In addition to the formulations as described above, the active peptide or chimeric peptide can also be formulated into a reservoir preparation. Such long-acting formulations can be administered by implantation (for example subcutaneous or intramuscular) or by intramuscular injection. Thus, for example, the compound can be formulated with a suitable polymeric or hydrophobic material (for example, formulated as an emulsion in an acceptable oil) or an ion exchange resin, or formulated as a sparingly soluble derivative, for example, a sparingly soluble salt.

Alternatively, other drug delivery systems can be used. The chimeric peptide can be delivered using liposomes and emulsions. Certain organic solvents, such as dimethyl sulfoxide, can also be used. Additionally, a compound can be delivered using a sustained release system, such as a semipermeable substrate of solid polymers containing a therapeutic agent.

Sustained release capsules may release the chimeric peptide for several weeks up to over 100 days depending on their chemical properties. Other strategies for stabilization of a protein can be used depending on the chemical property and biostability of a therapeutic agent.

In some embodiments, as the active peptides or chimeric peptides disclosed herein can contain charged side chains or termini, they can be included in any of the above formulations as a free acid or base or as a pharmaceutically acceptable salt. Pharmaceutically acceptable salts can be those which substantially retain the biological activity of a free base and are prepared by reaction with an inorganic acid. Pharmaceutical salts tend to be more soluble in water and other protic solvents than corresponding free base forms.

The active peptide or chimeric peptide is used in an amount effective to achieve the intended purpose (e.g., to reduce the damaging effect of stroke injuries and related conditions). A therapeutically effective amount means an amount of the active peptide or chimeric peptide sufficient to significantly reduce the injuries caused by stroke in patients (or a model animal population) treated with the active peptide or chimeric peptide disclosed herein, as compared with the central nervous system injury in a control population of patients (or model animals) not treated with the active peptide or chimeric peptide disclosed herein. If a treated patient achieves a better output as compared with a mean output (as determined by infarction volume or disability index) in a comparable patient control population not treated by the methods disclosed herein, the amount is also considered to be therapeutically effective. The amount is also considered to be a therapeutically effective amount. If a treated patient shows 2 or fewer disability scores in the Rankin scale and 75 or more scores in the Barthel scale, the amount is also considered to be a therapeutically effective amount. If a treated patient population shows a significantly improved (i.e., less disability) score distribution in the disability scale as compared with comparable untreated populations, the dose is also considered to be therapeutically effective, see Lees et al. N Engl J Med 2006; 354: 588-600. A therapeutically effective regimen represents a combination of a therapeutically effective dose and a administration frequency required to achieve the above intended purpose. Usually a single administration can be sufficient.

In some embodiments, a preferred dose range comprises 0.001 to 20 µmol of the active peptide or chimeric peptide per kg patient body weight within 6 hours after stroke, optionally 0.03 to 3 µmol of the active peptide or chimeric peptide per kg patient body weight. In some methods, 0.1-20 µmol of the active peptide or chimeric peptide per kg patient body weight is administered within 6 hours. In some methods, 0.1-10 µmol of the active peptide or chimeric peptide per kg patient body weight is administered within 6 hours, more preferably about 0.3 µmol of the active peptide or chimeric peptide per kg patient body weight is administered within 6 hours. In other instances, the dose range is 0.005 to 0.5 µmol of the active peptide or chimeric peptide per kg patient body weight. The dose per kg body weight can be converted from rats to humans by dividing by 6.2 to compensate for different surface area: mass ratios. In gram, suitable dose of the active peptide or chimeric peptide for human use may include 0.01 to 100 mg/kg patient body weight, or more preferably 0.01 to 30 mg/kg patient body weight or 0.01 to 10 mg/kg, or 0.01 to 1 mg/kg.

In some embodiments, the administered amount of the active peptide or chimeric peptide depends on the subject being treated, the weight of the subject, the pain severity, the administration mode, and the adjustments by the prescribing physician. The treatment can be repeated when the symptoms are detectable or even undetectable. The treatment can be provided alone or in combination with other drugs.

In some embodiments, a therapeutically effective dose of the active peptide or chimeric peptide disclosed herein is capable of providing a therapeutic benefit without causing significant toxicity. The toxicity of the chimeric peptide can be determined in cell cultures or experimental animals by standard pharmaceutical procedures, for example by determining $LD_{50}$ (a dose that kills 50% of the population) or $LD_{100}$ (a dose that kills 100% of the population). The dose ratio between toxic effect and therapeutic effect is the therapeutic index. Chimeric peptides or peptidomimetics exhibiting high therapeutic indexes are preferred (see, for example, Fingl et al, 1975, In: The Pharmacological Basis of Therapeutics, Chapter 1, page 1).

In some embodiments, the pharmaceutical composition is used for treating, ameliorating or preventing a nervous system injury or a disease or pain caused by the injury, or used as a neuroprotective agent. In some embodiments, the nervous system injury is one caused by excitatory neurotoxicity, wherein the injury is located in the peripheral nervous system or the central nervous system.

In some embodiments, the nervous system injury caused by excitatory neurotoxicity comprises an injury selected from the group consisting of a stroke or spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke. In some embodiments, the pharmaceutical composition is used for treating, ameliorating or preventing a nervous system injury caused by ischemic stroke.

Stroke is a condition caused by impaired blood flow in the CNS. Possible causes include embolism, bleeding, and thrombosis. Some neuronal cells die immediately due to impaired blood flow. These cells release their component molecules (including glutamic acid), which in turn activate the NMDA receptor, which increases intracellular calcium levels and intracellular enzyme levels, resulting in death of more neuronal cells (excitatory neurotoxicity cascade amplification). The death of CNS tissues is called as infarction. The infarction volume (i.e., the volume of dead neuronal cells in the brain caused by stroke) can be used as an indicator of the extent of pathological injuries caused by stroke. Symptomatic effects depend on both the infarction volume and the location of the infarction in the brain. The disability index can be used as a measure of symptomatic injuries, such as the Rankin Stroke Outcome Scale (Rankin, Scott Med J; 2: 200-15 (1957) and the Barthel Index. The Rankin Scale is based on a direct assessment of a patient's systemic condition as follows.

0: completely no symptom.

1: with symptoms, but no significant disability; able to perform all daily work and activities.

2: minor disability; unable to perform all previous activities, but able to take care of their own affairs without help.

3: moderate disability that requires some help, but able to walk without help.

4: moderate to severe disability, unable to walk without help, and unable to take care of their own body requirements without help.

5: severe disability; bedridden, incontinence, and requiring lasting care and attention.

The Barthel Index is based on a series of questions about the patient's ability to perform 10 basic daily living activities, which are scored between 0 and 100, with lower scores indicating more disability (Mahoney et al., Maryland State Medical Journal) 14:56-61 (1965).

Alternatively, stroke severity/output can be measured using the NIH Stroke Scale, which is available on the World Wide Web at ninds.nih.gov/doctors/NIH_Stroke_Scale_Booklet.pdf. The Scale is based on a patient's ability to perform 11 sets of functions, including assessment of a patient's consciousness, movement, feeling, and language function levels.

Ischemic stroke more clearly specifies a type of stroke caused by blockage of blood flow to the brain. The potential pathology for such blockages is most commonly associated with the occurrence of fat deposits along the walls of blood vessels. This condition is called as atherosclerosis. These fat deposits can cause two types of obstruction. Cerebral thrombosis refers to a thrombus (blood clot) formed in a blocked part of a blood vessel. "Brain embolism" usually means that various emboli in the blood (such as a wall thrombus in the heart, atherosclerotic plaque, fat, tumor cells, fibrocartilage or air) enter the cerebral artery along with blood flow to block blood vessels. When the collateral circulation is not sufficient for compensation, it causes ischemic necrosis of brain tissue to which the artery supplies blood, and focal neurologic impairment. The second important cause of embolism is an irregular heartbeat called arterial fibrillation. It causes a condition in which a blood clot can be formed in the heart, and then moves and transfers to the brain. Other potential causes of ischemic stroke are hemorrhage, thrombosis, arterial or venous severing, cardiac arrest, shock from any causes (including bleeding), and iatrogenic causes, such as direct surgical injuries to cerebral blood vessels or blood vessels going to the brain or cardiac surgery. Ischemic stroke accounts for approximately 83% of all stroke cases.

Several other neurological disorders can also cause neuron death through NDMAR-mediated excitatory neurotoxicity. These disorders include neurodegenerative diseases, anxiety, epilepsy, hypoxia, damage to the CNS irrelevant to stroke, such as traumatic brain injury and spinal cord injury. Accordingly, in some embodiments, the pharmaceutical composition is used for treating, ameliorating or preventing neurodegenerative diseases, anxiety or epilepsy, wherein the neurodegenerative diseases may comprise Alzheimer's disease, amyotrophic lateral sclerosis (ALS), Parkinson's disease or Huntington's disease.

In a fourth aspect, there is provided in the present application a method for treating, ameliorating or preventing a nervous system injury and a disease or pain associated with the injury, a neurodegenerative disease, anxiety or epilepsy, comprising administering to a subject in need thereof a peptide as described in the first aspect or a chimeric peptide as described in the second aspect, or a pharmaceutical composition as described in the third aspect.

In some embodiments, the nervous system injury caused by excitatory neurotoxicity comprise an injury selected from the group consisting of a stroke or spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the neurodegenerative disease includes Alzheimer's disease, amyotrophic lateral sclerosis (ALS), Parkinson's disease, or Huntington's disease.

In some embodiments, the subject is a subject suffering from ischemic stroke. In some embodiments, administration of a peptide as described in the first aspect of the present application, or a chimeric peptide as described in the second aspect, or a pharmaceutical composition as described in the third aspect, can reduce the volume of the cerebral infarction portion caused by cerebral ischemia.

In a fifth aspect, there is provided in the present application use of a peptide as described in the first aspect, or a chimeric peptide as described in the second aspect, or a pharmaceutical composition as described in the third aspect, in the preparation of a medicament for treating, ameliorating or preventing a nervous system injury and a disease or pain associated with the injury, a neurodegenerative disease, anxiety or epilepsy, or in the preparation of a neuroprotective agent.

In some embodiments, the a nervous system injury caused by excitatory neurotoxicity comprise an injury selected from the group consisting of a stroke or spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the neurodegenerative disease includes Alzheimer's disease, amyotrophic lateral sclerosis (ALS), Parkinson's disease, or Huntington's disease.

In some embodiments, the medicament is used for treating, ameliorating or preventing a nervous system injury caused by ischemic stroke.

It should be understood that the foregoing detailed description only aims to help those skilled in the art to more clearly understand the present application, but is not intended to limit the present application in any way. Those skilled in the art can make various modifications and changes to the described embodiments.

EXAMPLES

The following examples are provided only to illustrate some embodiments of the present application without any purpose or nature of limitation.

Example 1: Screening of Active Peptide Molecules

Based on reported study results, the Tat transmembrane peptide YGRKKRRQRRR (SEQ ID NO: 2) was selected and ligated to various numbers of amino acids to form a peptide library. The chimeric peptide molecules in the peptide library were tested for interaction with the PDZ1/2 domain expressed and purified in vitro, and the polypeptides were preliminarily screened for the strength of interaction force.

The immobile phase molecule (ligand) was PDZ1/2 protein with a molecular weight of approximately 20 kD at a concentration of 2 mg/ml. The mobile phase molecule (analyte) was a polypeptide to be screened with a molecular weight of approximately 2 kD at a concentration of 10 mg/ml. The CMS chip was used for fixation using a Biacore 3000 instrument. The electrophoresis buffer was PBS plus 0.005% Tween 20. Fixation was carried out using an amino coupling method. The concentration of the ligand was 10 µg/ml. The fixation buffer was 10 mM sodium acetate, pH 4.0. Fixed amount was 1400 RU, which was fixed to flow cell 2. The used flow rate was 10 µl/ml and the ligand was loaded for 1 minute. 10 mM Gly at pH 2.0+2.5 was used as a regenerant. Regeneration was carried out at a flow rate of 30 µl/min. The loading time was 30 s.

Kinetic analysis was performed using the following conditions.

control channel: flow cell 1;
electrophoresis buffer: PBS;
mode: Kinetic Analysis Wizard;
concentration gradients: 6.25n, 12.5n, 25n, 50n, 100n, 200n, 400 nM;
loading time: 1 minute;
dissociation time: 2 min; and
flow rate: 30 µl/min.

The data was fitted using the fitting software Biaevaluation 4.1. The fitting model was a 1:1 binding model. The dissociation constant KD value was inversely proportional to the interaction force.

By screening, a chimeric peptide having strong capability of interacting with the PDZ1/2 domain was obtained, and named as P5. The sequence of the chimeric peptide was shown below.

P5:
(SEQ ID NO: 3)
YGRKKRRQRRRYEKLLDTEI

In order to directly compare with a similar chimeric peptide in the reported studies, a control chimeric peptide NA-1 was introduced with the following sequence.

NA-1:

YGRKKRRQRRRKLSSIESDV (SEQ ID NO: 4)

Furthermore, by comparing P5 with NA-1 for their structural differences, a chimeric peptide YE-NA-1 having two residues of YE added to the N-terminus of the active peptide of the chimeric peptide NA-1 was additionally introduced, and its sequence is shown below.

YE-NA-1:

YGRKKRRQRRRYEKLSSIESDV (SEQ ID NO: 5)

The chimeric peptides NA-1, YE-NA-1 and P5 were simultaneously subjected to tests for interaction with the PDZ1/2 domain as mentioned above, and the results were shown in Table 1 below.

TABLE 1

Detection of interaction force between three chimeric peptides and PDZ1/2 domain

| chimeric peptides | NA-1 | YE-NA-1 | P5 |
| --- | --- | --- | --- |
| KD (M) | 7.53E−08 | 5.44E−08 | 2.99E−08 |

As shown in Table 1, the chimeric peptides YE-NA-1 and P5 interacted more strongly with the PDZ1/2 domain as compared with the control chimeric peptide NA-1, and the performance of P5 was even better. Therefore, based on the inventors' speculation, the additional two amino acid residues YE at the N-terminus of the active peptide caused certain improved effect on the interaction of the polypeptide with the PDZ1/2 domain. Furthermore, P5 lacked two weakly hydrophobic serines (SS) relative to the carboxy terminus of YE-NA-1. Based on the inventors' speculation, this may further increase the interaction of the polypeptide with the PDZ1/2 domain.

The chimeric peptide P5 was selected for further testing in the following experiments, and in some experiments, NA-1 and YE-NA-1 were used as controls.

Example 2: Pull-Down Assay to Verify the Interaction of P5 with PDZ1/2 Domain

To confirm that P5 can interact with the PDZ1/2 domain, a pull-down assay was performed.

The column was equilibrated with 100 μl of His beads and 1 ml of MCAC-0 buffer for 5 min and shaked at 4° C. The mixture was centrifuged at 5000 g for 1 minute at 4° C., and the supernatant was discarded. 1 mg of PDZ1/2 protein was added to the mixture, and a buffer was added to reach the volume of 1 ml. The mixture was spun for binding for 1 hour at 4° C. The mixture was centrifuged at 5000 g for 1 minute at 4° C., and the supernatant was discarded. The mixture was washed three times with 1 ml of MCAC-0 buffer for 5 minutes each time (at 4° C., washing with shaking). 1 mg of P5 protein was added to the mixture, and a buffer was added to reach the volume of 1 ml. The mixture was spun for binding for 2 hours at 4° C. The mixture was centrifuged at 5000 g for 1 minute at 4° C., and the supernatant was discarded. The mixture was washed three times with 1 ml of lysis buffer for 5 minutes each time (at 4° C., washing with shaking). 20 μl of MCAC-300 was added after washing. After centrifugation, the eluate was taken for a SDS-PAGE assay. The experimental results were shown in FIG. 1.

As shown in FIG. 1, both P5 and the PDZ1/2 domain were contained in the eluted band of the chimeric peptide P5, thereby confirming that the chimeric peptide P5 can bind to the PDZ1/2 domain.

Example 3: Therapeutic Effect of Chimeric Peptide on MCAO Model Rat

Preparation Method and Scoring Standard of MCAO

The focal cerebral ischemia-reperfusion model was prepared according to the reversible middle cerebral artery occlusion (MCAO) suture method proposed by Longa with modifications in view of the anatomical structure of the rat brain. The rats were anesthetized by intraperitoneal administration of 10% chloral hydrate at a dose of 0.3 ml/kg. After anesthetization, a cut was created at the cervical midline, and the common carotid artery (CCA), external carotid artery (ECA) and pterygopalatine artery were exposed. The head portion (0.5 cm) of a monofilament nylon fishing line (0.26 mm) was coated with paraffin and a mark was made at 20 mm. All rats were inserted through the right CCA incision, and the pterygopalatine artery was temporarily clamped to prevent mis-insertion. The length of the occlusion line was about 18-20 mm from the bifurcation of CCA depending on the animal's weight, thereby occluding middle cerebral artery on the right side. The skin was then sewed, and the tail end of the occlusion line was partially fixed to the skin. After a period of ischemia for 2 hours, the occlusion line was carefully pulled out to form a reperfusion. The procedure steps for the sham control were the same as the surgery group, except for insertion of a nylon fishing line. The body temperature was maintained at 37±0.5° C. during the ischemia period and 2 h after reperfusion. The success marker for the model is that the rats, after they awoke from anesthesia, showed paralyzed left limb, unstable standing and turning to one side when their tails were lift up.

The neurological defect signs were scored according to Longa and Bederson's 5-score method at 24 h after the animals awoke from anesthesia.

0: no symptom of nerve damage;
1: unable to fully extend the contralateral fore paw;
2: turning to the opposite side;
3: dumping to the opposite side;
4: unable to spontaneously walk and loss of consciousness.

The higher the score was, the severer the animal's behavioral disorder was.

Experimental Animals and Materials

The used animals were male adult SD rats (Vittalia) of SPF grade with body weight of 220-250 g.

The used instruments included one line scissor, two eye surgery scissors, four curved forceps, 4#, 5# surgical sutures, 6×17 triangular needles, a occlusion line (0.26 mm of diameter), and one needle holders. The used agents included Enbipu sodium chloride injection solution (Shijiazhuang Group NBP Pharmaceutical Co., Ltd.), chloral hydrate, furosemide (20 mg/vial), gentamicin sulfate (80 mg/vial), cotton swabs, and medical trays. The test peptides were synthesized by Kingsray Biotech Inc.

Experimental Grouping

The experimental animals were divided into the negative control group, sham group, model group, positive drug Enbipu group, NA-1 group, YE-NA-1 group and P5 group. A saline solution, positive drug Enbipu, NA-1 (10 mg/kg), YE-NA-1 (10 mg/kg) and P5 (10 mg/kg, 3 mg/kg and 1 mg/kg) were respectively administered to individual group of rats via tail vein injection at 1 hour after ischemia. No drugs were administered to the normal group and the sham group.

Calculation of Infarction Volume

The rats were sacrificed by decapitation after scoring. The brain tissues were quickly removed and placed in a refrigerator at −20° C. After 10 minutes, the tissues were placed in a room temperature environment. The brains were placed in a rat brain section mold. After the olfactory bulb, cerebellum and low brain stem were removed, the brains were coronally cut five times at 2 mm thickness as shown in the profile to obtain six continuous raw coronal slices. Then, the brain sections were quickly placed in a 5 ml solution containing 2% TTC, and incubated at 37° C. for 30 minutes in the dark, during which the brain sections were flipped once every 5 minutes. With the TTC staining, the normal tissue would be rose red, and the infarcted tissue would be unstained and retained white. Each group of brain sections was arranged neatly, and photographed. The photos were processed by an image analysis system software and statistically analyzed. The infarction area of each brain section was calculated, and multiplied by the thickness of each brain section (2 mm). The products of the infarction area of individual brain section multiplied by the thickness were summed to obtain the cerebral infarction volume for each animal. The volumes were expressed as percentages accounting for the cerebral hemisphere to eliminate the effects of cerebral edema.

Experimental Results

Figure 2:
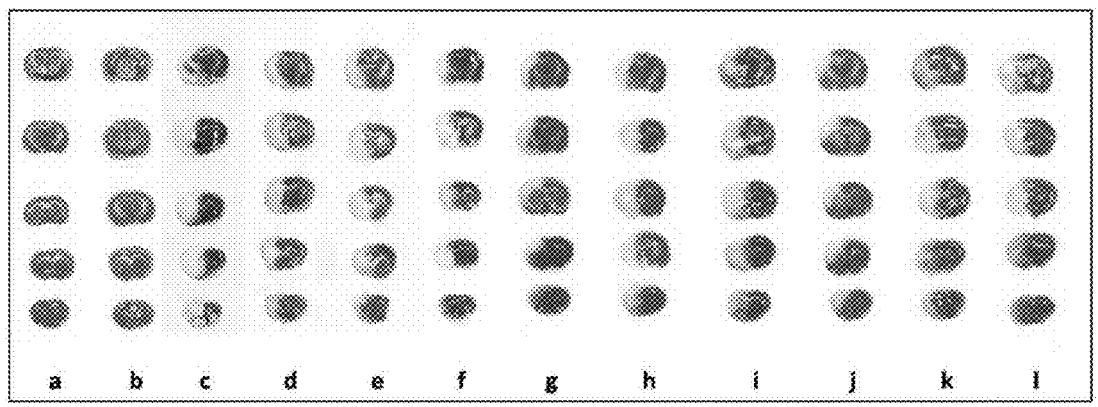
FIG. 2 shows TTC staining images of brain sections from MCAO model rats treated with polypeptide P5. a. normal group; b. sham group; c. model group; d. positive control drug (Enbipu injection solution) group; e. NA-1 at a dose of 10 mg/kg body weight; f YE-NA-1 at a dose of 10 mg/kg body weight; g. P5 at a dose of 10 mg/kg body weight; h. P5 at a dose of 3 mg/kg body weight; i. P5 at a dose of 1 mg/kg body weight; j. prophylactic administration of P5 at a dose of 10 mg/kg body weight; k. prophylactic administration of P5 at a dose of 3 mg/kg body weight; l. prophylactic administration of P5 at a dose of 1 mg/kg body weight.
Figure 3:
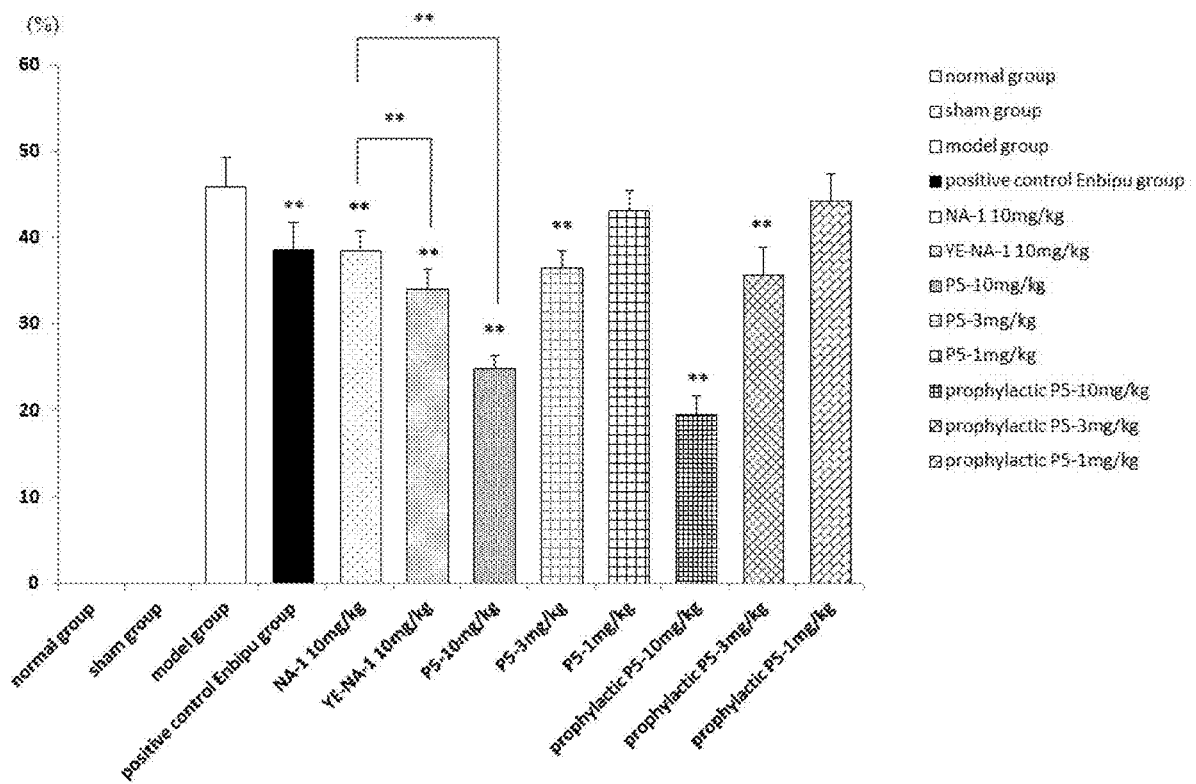
FIG. 3 is a graph showing the statistical data of cerebral infarction volume after therapeutic and prophylactic administration of polypeptide P5 at various doses to MCAO model rats. **p<0.01.

The experimental results were shown in FIG. 2. A statistic histogram of cerebral infarction volume data as shown in FIG. 3 was plotted based on statistical analysis of the data of the cerebral infarction volume in FIG. 2, and specific statistical data of the cerebral infarction volume were provided in Table 2 below. The results showed that the therapeutic administration and prophylactic administration of the highest dose (10 mg/kg) of P5 could significantly reduce the cerebral infarction volume of rats undergoing cerebral ischemia by about 50% ($p<0.01$), while the positive drug Enbipu injection group was only observed a reduction by about 16% ($p<0.01$), the NA-1 group was observed a reduction about 16% ($p<0.01$), and the YE-NA-1 group was was observed a reduction by about 26% ($p<0.01$). The therapeutic administration and prophylactic administration of the second highest dose (3 mg/kg) of P5 also desirably reduced the cerebral infarction volume. In addition, the data showed that the infarction volume value decreased with the increasing dose of P5, which indicated that the therapeutic effect was positively correlated with the drug dose. The therapeutic effect of the polypeptide YE-NA-1 was significantly better than that observed for NA-1. Based on the inventors' speculation, the addition of two amino acids YE may lead to a better therapeutic effect than NA-1 by improving the interaction of the polypeptide with the PDZ1/2 domain.

TABLE 2

Therapeutic effect of the polypeptide P5 on MCAO model rats

| Groups | Mean of infarction volume percentage (%) | Standard deviation | Reduction of infarction volume percentage vs model group | T test vs model group | T test vs P5 at 10 mg/kg |
| --- | --- | --- | --- | --- | --- |
| Normal group | 0 | 0 | | | |
| Sham group | 0 | 0 | | | |
| Model group | 45.96 | 3.35 | | | |
| Positive drug Enbipu group | 38.61 | 3.21 | 15.99 | $p<0.01$ | |
| NA-1 10 at mg/kg | 38.56 | 2.25 | 16.10 | $p<0.01$ | $p<0.01$ |
| YE-NA-1 at 10 mg/kg | 33.96 | 2.40 | 26.11 | $p<0.01$ | $p<0.01$ |
| P5 at 10 mg/kg | 24.84 | 2.90 | 45.95 | $p<0.01$ | |
| P5 at 3 mg/kg | 36.54 | 2.35 | 20.50 | $p<0.01$ | |
| P5 at 1 mg/kg | 43.22 | 3.12 | 5.96 | 0.061 | |
| prophylactic administration of P5 at 10 mg/kg | 19.54 | 2.30 | 57.48 | $p<0.01$ | |
| prophylactic administration of P5 at 3 mg/kg | 35.66 | 1.50 | 22.41 | $p<0.01$ | |
| prophylactic administration of P5 at 1 mg/kg | 44.23 | 2.20 | 3.76 | 0.082 | |

Example 4: Distribution of P5 in Rat Brain

Figure 4:
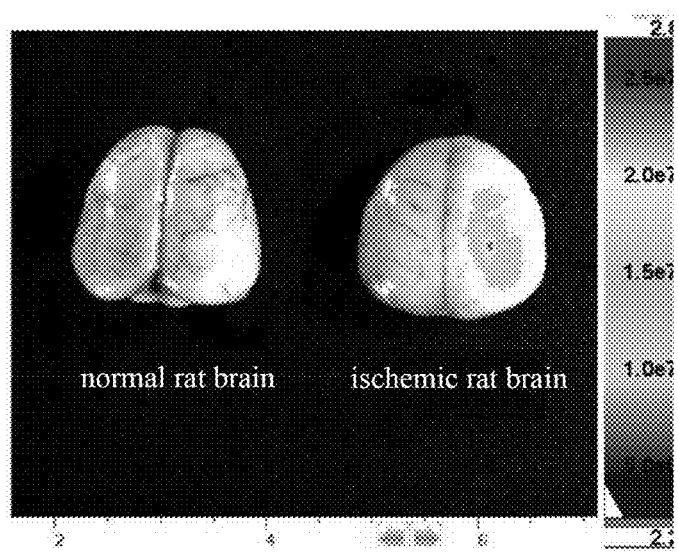
FIG. 4 shows the distribution of polypeptide P5 in rat brains.
Figure 5:
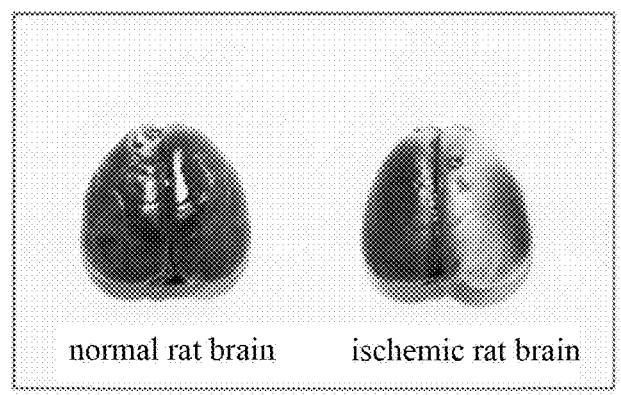
FIG. 5 shows TTC staining images of rat brains.

The normal control rats and MCAO model rats were respectively injected via tail vein with a saline solution containing fluorescently labeled polypeptide FITC-P5 (10 mg/kg) at 1 hour after modeling. The rats were sacrificed 12 hours after the administration. The brain tissues were quickly removed and placed in a small animal living body imaging system for fluorescence detection. After the fluorescence detection was completed, the brain tissues were placed in the TTC dye solution for staining to determine the correlation between the ischemic area and the drug distribution. As shown in FIGS. 4 and 5, the normal rat brain could be completely stained by TTC and there was no distribution of the fluorescently labeled polypeptide, while the ischemic region of the ischemic rat brain could not be stained by TTC, and the fluorescently labeled polypeptide was distributed in the ischemic region with the middle artery region being the core ischemic region, suggesting that the polypeptide P5 could target the ischemic region and exert therapeutic effect, and its distribution amount was positively correlated with the ischemia degree.

Example 5: HE Staining for Observation of Histological Changes

The rats in each group were decapitated at 24 h after ischemia, and the resultant brain was coronally sectioned near the optic chiasm with a thickness of about 4 mm. The sections were fixed with 10% formalin solution and dehydrated with alcohol with a concentration gradient from 70% to 100%. The sections were permeabilized twice in xylene, and embedded in paraffin. The paraffin block was carefully trimmed, and immobilized on a paraffin slicing machine, and sliced to sections with a thickness of 4 µm. The paraffin sections were completely unfolded, attached to a clean and dry glass slide, and stored in a refrigerator at 4° C. Conventional HE staining was performed, and the staining results were observed by light microscopy.

Figure 6:
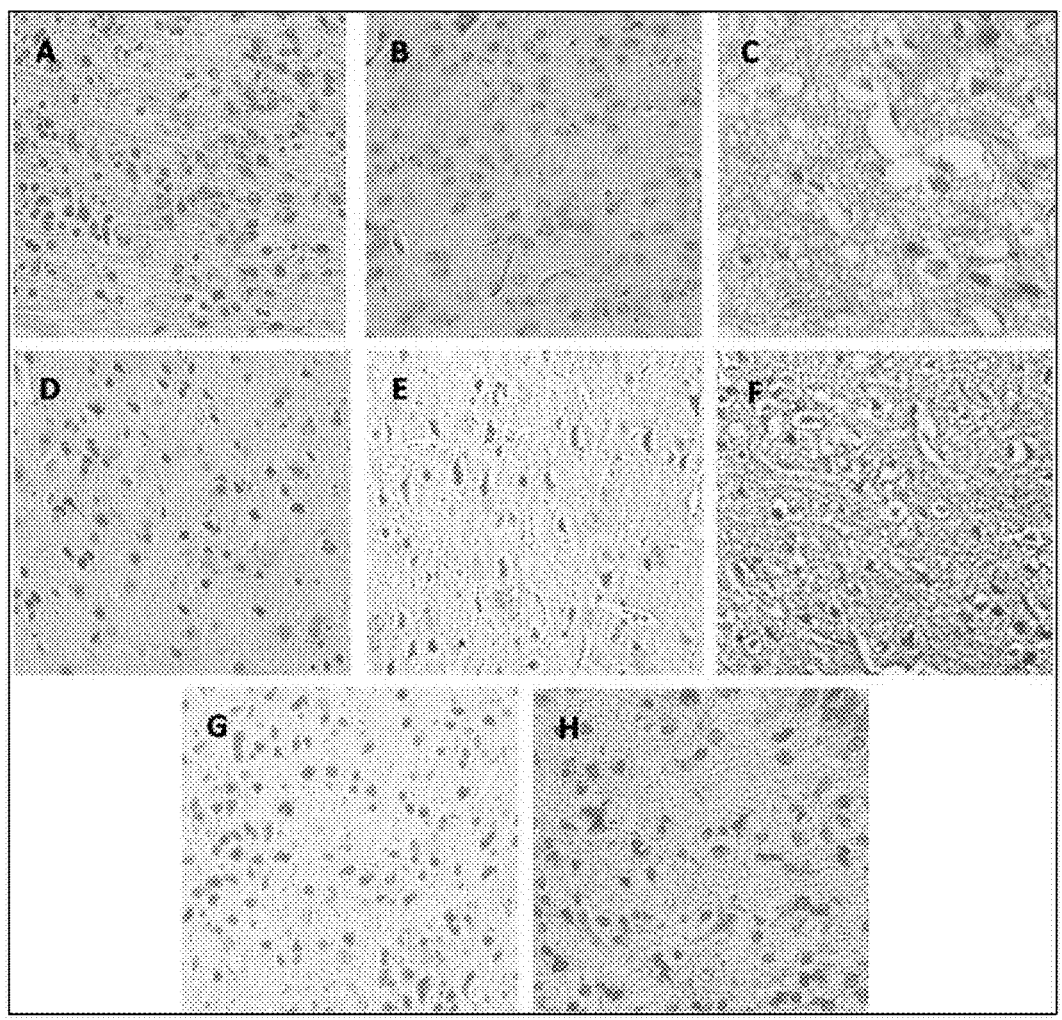
FIG. 6 shows HE staining images of paraffin sections of rat brains. A: normal group, B: sham group, C: model group, D: positive control administration group, E: NA-1, F: YE-NA-1 group, G: P5 group, H: P5 prophylactic administration group.

The experimental results were shown in FIG. 6. The nerve cells of the normal brain tissue showed a clear nucleus, a round nuclear, and an intact nuclear membrane. The brain tissues at the ischemic side of the ischemic model group rats showed severe neuronal cell necrosis, cell swelling, nuclear condensation, loose and light stained cytoplasm, and vacuolization. For therapeutic administration group and prophylactic administration group of P5 at 10 mg/kg, the above pathological changes were significantly improved, and the results were better than the administration groups of the positive drug Enbipu injection solution, NA-1 and YE-NA-1 (10 mg/kg).

Example 6: Acute Toxicity Assessment

Acute toxicity tests were performed on rats. The results showed that P5 had no lethal effect and other obvious toxic side effects on the rats at a dose of 200 mg/kg body weight.

All publications and patent documents cited in the Specification are herein incorporated by reference as if each publication or patent were specifically and individually indicated to be incorporated by reference. Various changes and equivalent substitutions can be made to the various embodiments disclosed herein without departing from the true spirit and scope of the disclosure. Any feature, step or embodiment of an embodiment of the present disclosure can be used in combination with any other feature, step or embodiment, unless otherwise stated in the context.

The invention claimed is:

1. A peptide comprising the amino acid sequence YEKLLDTEI (SEQ ID NO: 1) or comprising the amino acid sequence identical to YEKLLDTEI (SEQ ID NO: 1) except for one or more conservative amino acid substitutions selected from the group consisting of a substitution between D and E, a substitution among L, V and I, and a substitution between T and S, wherein the peptide is capable of binding to the PSD-95/Discs-large/ZO-1 1/2 domain (PDZ1/2 domain) of postsynaptic density 95 protein (PSD-95) and inhibits the interaction between N-methyl-D-aspartic acid receptor (NMDAR) and PSD-95.

2. The peptide of claim 1, wherein the peptide comprises the amino acid sequence identical to YEKLLDTEI (SEQ ID NO: 1) except for one or more conservative amino acid substitutions in LDTEI (SEQ ID NO: 6) selected from the group consisting of a substitution between D and E, a substitution among L, V and I, and a substitution between T and S.

3. The peptide according to claim 2, wherein the peptide comprises the amino acid sequence identical to YEKLLDTEI (SEQ ID NO: 1) except for a replacement of LDTEI (SEQ ID NO: 6) with a sequence selected from the group consisting of LDTEL (SEQ ID NO: 7), LDTEV (SEQ ID NO: 8), LDTDI (SEQ ID NO: 9), LDTDL (SEQ ID NO: 10), LDTDV (SEQ ID NO: 11), LDSEI (SEQ ID NO: 12), LDSEL (SEQ ID NO: 13), LDSEV (SEQ ID NO: 14), LDSDI (SEQ ID NO: 15), LDSDL (SEQ ID NO: 16), LDSDV (SEQ ID NO: 17), LETEI (SEQ ID NO: 18), LETEL (SEQ ID NO: 19), LETEV (SEQ ID NO: 20), LETDI (SEQ ID NO: 21), LETDL (SEQ ID NO: 22), LETDV (SEQ ID NO: 23), VDTEI (SEQ ID NO: 24), VDTEL (SEQ ID NO: 25), VDTEV (SEQ ID NO: 26), VDTDI (SEQ ID NO: 27), VDTDL (SEQ ID NO: 28), VDTDV (SEQ ID NO: 29), IDTEI (SEQ ID NO: 30), IDTEL (SEQ ID NO: 31), IDTEV (SEQ ID NO: 32), IDTDI (SEQ ID NO: 33), IDTDL (SEQ ID NO: 34), IDTDV (SEQ ID NO: 35), IETEI (SEQ ID NO: 36), IETEL (SEQ ID NO: 37), IETEV (SEQ ID NO: 38), IETDI (SEQ ID NO: 39), IETDL (SEQ ID NO: 40), and IETDV (SEQ ID NO: 41).

4. A chimeric peptide comprising an active peptide and an internalization peptide, wherein the active peptide is a peptide according to claim 1, and the internalization peptide facilitates uptake of the chimeric peptide by a cell.

5. The chimeric peptide of claim 4, wherein the internalization peptide comprises the amino acid sequence YGRKKRRQRRR (SEQ ID NO: 2).

6. The chimeric peptide of claim 5, comprising the amino acid sequence YGRKKRRQRRRYEKLLDTEI (SEQ ID NO: 3).

7. A pharmaceutical composition comprising a chimeric peptide of claim 4, and a pharmaceutically acceptable carrier.

8. A method for treating or ameliorating a condition selected from the group consisting of a nervous system injury, a related condition or pain caused by the injury, a neurodegenerative disease, anxiety and epilepsy in a mammal, comprising administering to a subject in need thereof a chimeric peptide of claim 4.

9. The method of claim 8, wherein the condition is stroke or a nervous system injury caused by stroke.

10. The method of claim 9, wherein the stroke is ischemic stroke, hemorrhagic stroke, or hemorrhagic stroke converted from ischemic stroke.

11. The method of claim 8, wherein the nervous system injury is a nervous system injury caused by excitatory neurotoxicity.

12. The method of claim 8, wherein the injury or pain is located in the peripheral nervous system or the central nervous system.

13. The method of claim 8, wherein the nervous system injury caused by excitatory neurotoxicity comprises an injury selected from the group consisting of a stroke or spinal cord injury, an ischemic or traumatic injury to a brain or spinal cord, an injury to a neuron in central nervous system (CNS) including an acute CNS injury, a hypoxia, ischemia, or mechanical injury and an injury caused by a neurodegenerative disease, anxiety, epilepsy or stroke.

14. The method of claim 8, wherein the neurodegenerative disease comprises Alzheimer's disease, amyotrophic lateral sclerosis (ALS), Parkinson's disease or Huntington's disease.

15. A pharmaceutical composition comprising a peptide of claim 1, and a pharmaceutically acceptable carrier.

16. A method for treating or ameliorating a condition selected from the group consisting of a nervous system injury, a related condition or pain caused by the injury, a neurodegenerative disease, anxiety and epilepsy in a mammal, comprising administering to a subject in need thereof a peptide of claim 1.

17. The method of claim 16, wherein the condition is stroke or a nervous system injury caused by stroke.

18. The method of claim 17, wherein the stroke is ischemic stroke, hemorrhagic stroke, or hemorrhagic stroke converted from ischemic stroke.

19. The method of claim 16, wherein the nervous system injury is a nervous system injury caused by excitatory neurotoxicity.

20. The method of claim 16, wherein the injury or pain is located in the peripheral nervous system or the central nervous system.

21. The method of claim 16, wherein the nervous system injury caused by excitatory neurotoxicity comprises an injury selected from the group consisting of a stroke or spinal cord injury, an ischemic or traumatic injury to a brain or spinal cord, an injury to a neuron in central nervous system (CNS) including an acute CNS injury, a hypoxia, ischemia, or mechanical injury and an injury caused by a neurodegenerative disease, anxiety, epilepsy or stroke.

22. The method of claim 16, wherein the neurodegenerative disease comprises Alzheimer's disease, amyotrophic lateral sclerosis (ALS), Parkinson's disease or Huntington's disease.

* * * * *